United States Patent [19]

Evans et al.

[11] Patent Number: 5,169,002
[45] Date of Patent: Dec. 8, 1992

[54] HEART PACEMAKER WIRE PROTECTOR DEVICE

[76] Inventors: Michael J. Evans; Marcia E. Tyler-Evans, both of 906 Annabelle Ave., Modesto, Calif. 95350

[21] Appl. No.: 670,179

[22] Filed: Mar. 15, 1991

[51] Int. Cl.$^5$ .................. A61B 17/06; B65D 73/02; B65D 25/00
[52] U.S. Cl. .................. 206/438; 206/813; 206/329; 206/331; 206/45.34
[58] Field of Search .............. 206/329, 331, 438, 813; 128/772, 785

[56] References Cited

U.S. PATENT DOCUMENTS

| | | | |
|---|---|---|---|
| 4,883,070 | 11/1989 | Hanson | 128/785 |
| 4,907,592 | 3/1990 | Harper | 128/419 P |
| 4,917,104 | 4/1990 | Rebell | 128/772 |

Primary Examiner—William I. Price
Attorney, Agent, or Firm—Leon Gilden

[57] ABSTRACT

An organization including an elongate, flexible web mounting medially of its length a transparent cylinder defined by a predetermined length less than that of the web, wherein each web accordingly includes a respective first and second flap overlying respective first and second ends of the cylinder, wherein each first and second flap includes a respective first and second hook and loop fastener surface coextensive therewith. The cylinder includes a respective second and third hook and loop fastener surface mounted to an exterior surface of the cylinder diametrically opposed to that of the web to receive and secure a respective flap thereon. The cylinder includes a respective blind bore directed interiorly of the cylinder from each end of a length less than that of the cylinder, wherein the tubes are arranged offset and parallel relative to one another. Each tube includes an associated indicator marker and receives an associated wire of a pacemaker, notably the atrial wire leads and the ventricular wire leads.

6 Claims, 3 Drawing Sheets

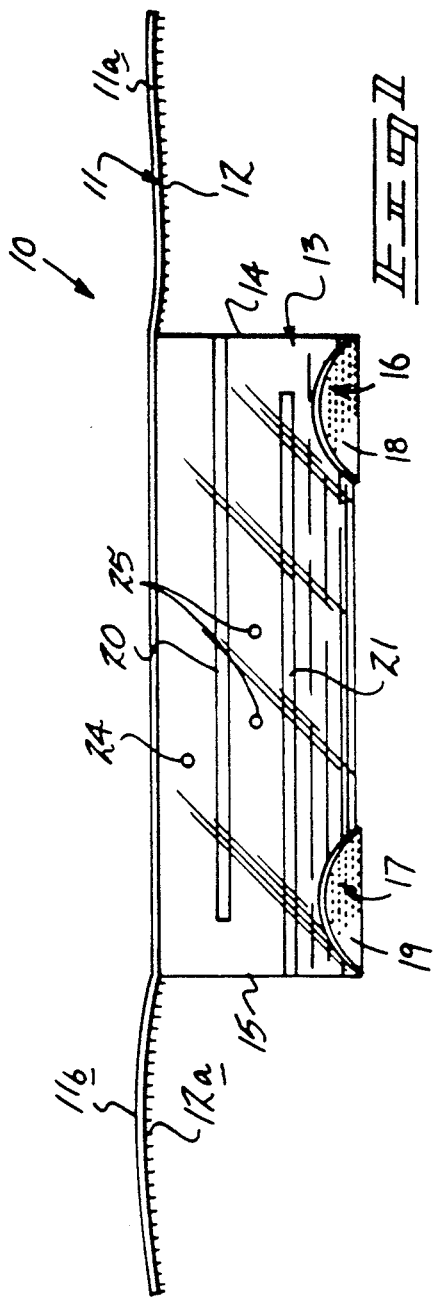
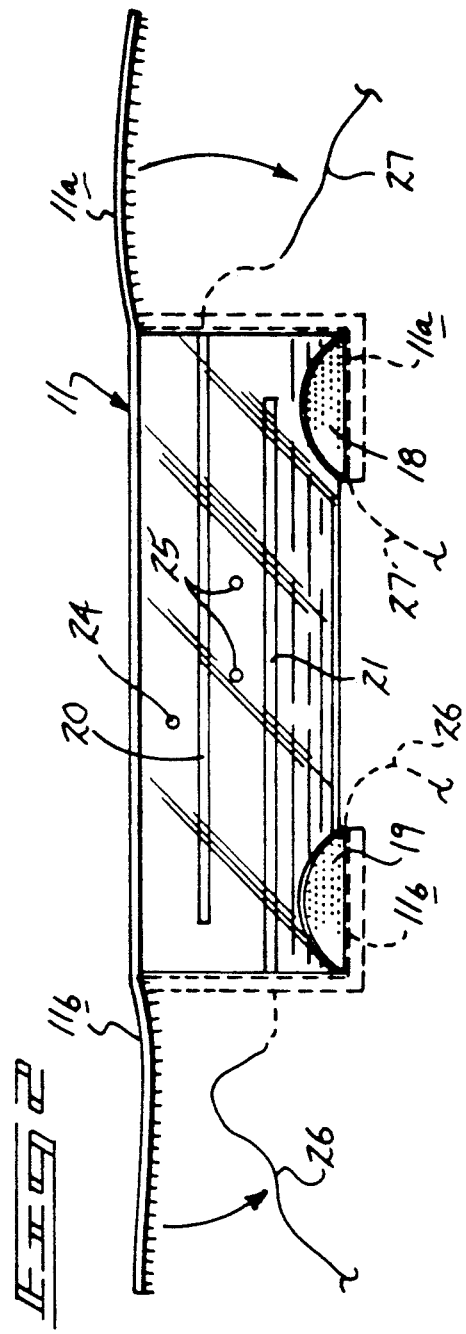

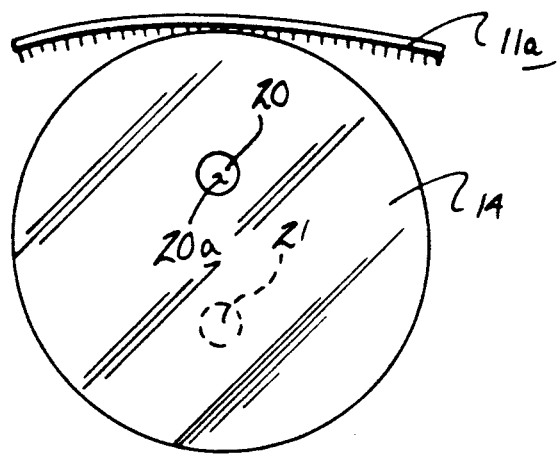
FIG 3
FIG 4
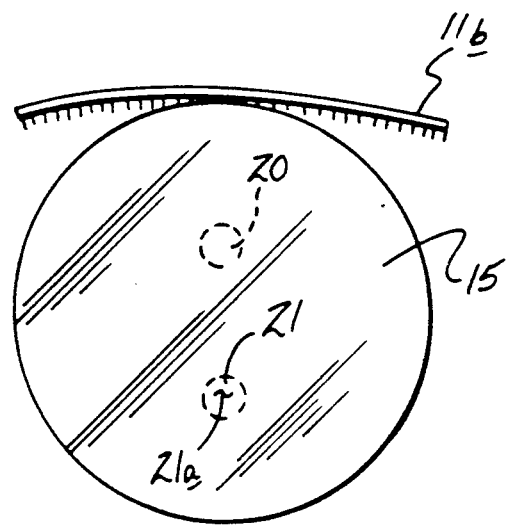

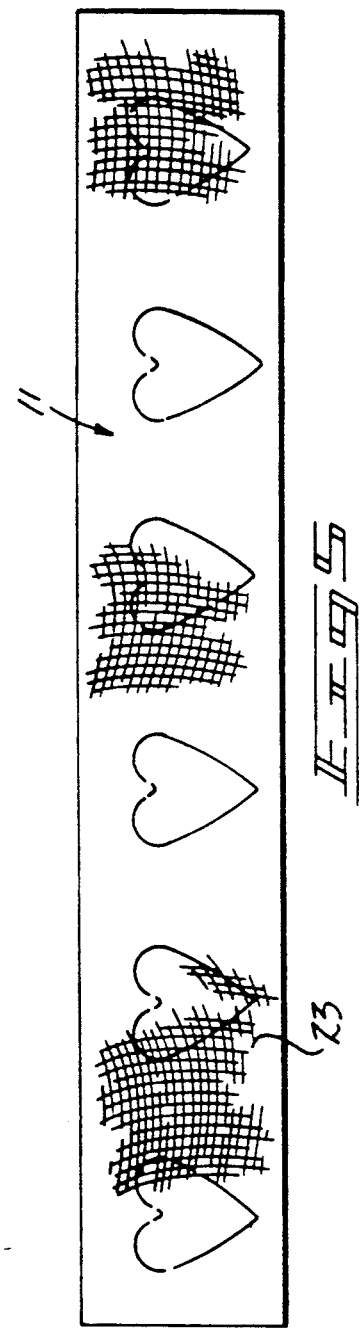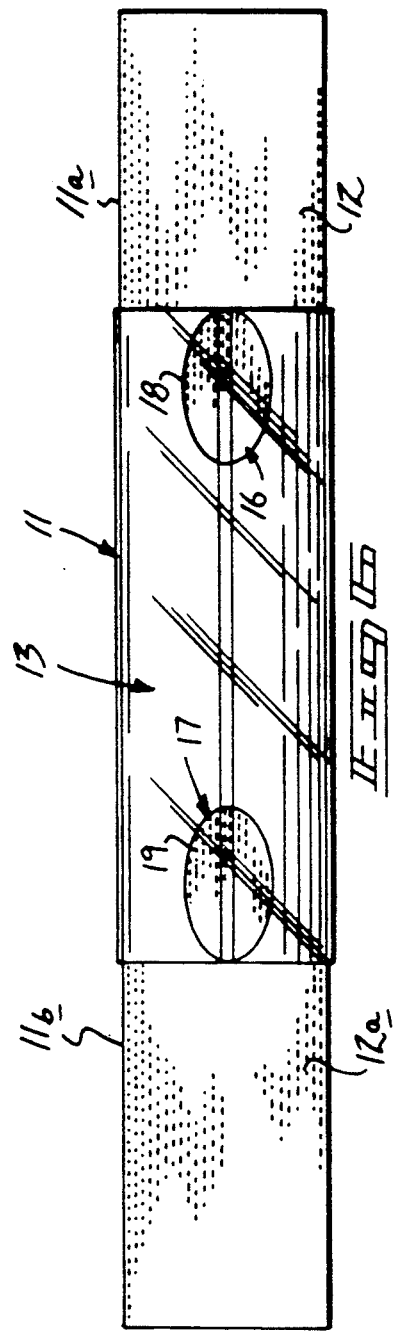

HEART PACEMAKER WIRE PROTECTOR DEVICE

BACKGROUND OF THE INVENTION

1. Field of the Invention

The field of invention relates to storage apparatus, and more particularly pertains to a new and improved heart pacemaker wire protector device wherein the same provides temporary storage and protection of wires associated with a pacemaker unit prior to mounting to an associated pacemaker relative to a patient.

2. Description of the Prior Art

In the application of temporary pacemakers external to an individual, the atrial wires and the ventricular wires are active in their insulative separation relative to one another and to various grounding surfaces is a necessity. To this end, the instant invention attempts to provide a convenient and efficient protective device for temporary storage of the wires prior to their final assembly to an external pacemaker unit after open heart surgery procedure for example. Insulative devices have been utilized in the prior art for providing such insulation of wires, but have heretofore failed to provide the convenient mounting as required by the instant invention. Examples of the prior art include U.S. Pat. No. 4,907,592 to Harper setting forth a connector for use in a catheter to a body implantable device utilizing an insulative, highly viscous material for use in moist environments.

U.S. Pat. No. 4,917,104 to Rebell sets forth an electrically insulated stiffener wire assemblage.

U.S. Pat. No. 4,883,070 to Hanson sets forth endocardial pacing lead for establishing electrical connection between heart tissue and a pacemaker and other heart management for monitoring devices.

As such, it may be appreciated that there continues to be a need for a new and improved heart pacemaker wire protector device as set forth by the instant invention which addresses both the problems of ease of use as well as effectiveness in construction in temporary mounting and storage of pacemaker wires therewithin and in this respect, the present invention substantially fulfills this need.

SUMMARY OF THE INVENTION

In view of the foregoing disadvantages inherent in the known types of wire storage apparatus now present in the prior art, the present invention provides a heart pacemaker wire protector device wherein the same temporarily receives and fixedly secures the atrial and the ventricular wires relative to an associated pacemaker. As such, the general purpose of the present invention, which will be described subsequently in greater detail, is to provide a new and improved heart pacemaker wire protector device which has all the advantage of the prior art wire protective apparatus and none of the disadvantages.

To attain this, the present invention provides an organization including an elongate, flexible web mounting medially of its length a transparent cylinder defined by a predetermined length less than that of the web, wherein each web accordingly includes a respective first and second flap overlying resepctive first and second ends of the cylinder, wherein each first and second flap includes a respective first and second hook and loop fastener surface coextensive therewith. The cylinder includes a respective second and third hook and loop fastener surface mounted to an exterior surface of the cylinder diametrically opposed to that of the web to receive and secure a respective flap thereon. The cylinder includes a respective blind bore directed interiorly of the cylinder from each end of a length less than that of the cylinder, wherein the tubes are arranged offset and parallel relative to one another. Each tube includes an assoicated indicator marker and receives an associated wire of a pacemaker, notably the atrial wire leads or the ventricular wire lead.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved heart pacemaker wire protector device which has all the advantages of the prior art wire protective apparatus and none of the disadvantages.

It is another object of the present invention to provide a new and improved heart pacemaker wire protector device which may be easily and efficiently manufactured and marketed.

It is a further object of the present invention to provide a new and improved heart pacemaker wire protector device which is of a durable and reliable construction.

An even further object of the present invention is to provide a new and improved heart pacemaker wire protector device which is susceptible of a low cost of manufacture with regard to both materials and labor, and which accordingly is then susceptible of low prices of sale to the consuming public, thereby making such heart pacemaker wire protector devices economically available to the buying public.

Still yet another object of the present invention is to provide a new and improved heart pacemaker wire protector device which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic side view of the invention.

FIG. 2 is an orthographic side view of the invention relative to the pacemaker wires to be directed therewithin.

FIG. 3 is an orthographic right side view of the instant invention.

FIG. 4 is an orthographic left side view of the instant invention.

FIG. 5 is an orthographic top view of the invention.

FIG. 6 is an orthographic bottom view of the invention.

DESCRIPTION OF THE PREFERRED EMBODIMENT

With reference now to the drawings, and in particular to FIGS. 1 to 6 thereof, a new and improved heart pacemaker wire protector device embodying the principles and concepts of the present invention and generally designated by the reference numeral 10 will be described.

More specifically, the heart pacemaker wire protector device 10 of the instant invention essentially comprises an elongate, flexible web 11 defined by a predetermined length mounting medially of its predetermined length a transparent cylinder 13. The cylinder 13 is mounted coextensively along an exterior surface thereof, with its exterior surface contiguously mounted to the web 11. The first flap 11a and the second flap 11b project exteriorly of each respective right and left circular end wall 14 and 15 of the cylinder 13. The first flap 11a includes a first hook and loop fastener surface formed coextensively thereof in confronting relationship relative to the right circular end wall 14, with a second hook, and loop fastener surface 12a mounted coextensively to the second flap 11b in confronting relationship relative to the left circular end wall 15. A first fastener patch 16 is mounted to the circular side wall of the transparent cylinder 13 adjacent the right circular end wall 14 diametrically opposed to the web 11. A second fastener patch 17 is mounted aligned with the first fastener patch 16 adjacent the left circular end wall 15 diametrically opposed to the web 11, as illustrated. The respective first and second fastener patches 16 and 17 have coextensively formed to an exterior surface thereof a respective third and fourth hook and loop fastener surface 18 and 19 that are respectively cooperative with the first and second hook and loop fastener surfaces 12 and 12a, as illustrated in FIG. 2 in phantom. A positive wire 26 and a negative atrial (or ventricular) wire 27 are each directed relative to a pacemaker apparatus (not shown) prior to their mounting to the pacemaker apparatus and are accordingly requried to be insulatively separated relative to one another. To this end, the cylinder 13 includes a first tube 20 directed into the cylinder and defined by a tube length less than the cylinder length, including an entrance opening 20a, formed through the right circular end wall 14. A second tube 21 positioned underlying the first tube 20 includes an entrance opening 21a directed through the left circular end wall 15, with the second tube 21 defined by a tube length less than the cylinder length. A positive atrial wire 26 and a negative atrial wire 27 are provided and each directed within a respective one of the first and second tubes 20 and 21 for positioning and insulative storage therebetween. Upon positioning of each respective wire 26 and 27 within an associated tube, the flaps 11a and 11b are directed downwardly to a phantom position, as illustrated in FIG. 2 with the first flap 11a secured to the first fastener patch 16 and the second flap 11b secured to the second fastener patch 17 for fixedly positioning and securing the wires within a transparent cylinder 13. The transparency of the cylinder provides readily available visual indication of the wires and their positioning within the respective tubes. Further, a first indicator 24 is associated with the first cylinder for providing visual indication of the atrial wire, with a second indicator 25 imposed on the second cylinder to provide indication of the ventricular wire to ensure the required distinction between the wires and providing their efficient and safe assembly subsequent to their storage within the cylinder.

FIG. 5 illustrates a top view of the web 11 and the use of an optional fifth hook and loop fastener surface 23 formed coextensively to the top surface of web to permit securement of the web for storage of the web and container.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principle of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A heart pacemaker wire protector device comprising,
    an elongate, flexible web defined by a predetermined web length, and
    an elongate cylinder defined by a cylinder length less than the web length mounted medially of the web coextensively of the cylinder, the cylinder including a right circular end wall and a left circular end wall, and the flexible web including a first flap extending beyond the cylinder overlying the right circular end wall, and a second flap extending beyond the cylinder overlying and extending beyond the left end wall, and a first storage tube directed in the cylinder extending from the right circular end wall interiorly of the cylinder, and a second storage tube within the cylinder extending from the left circular end wall, and each storage tube defined by a storage tube length less than the cylinder length.

2. An apparatus as set forth in claim 1 wherein the first flap includes a first hook and loop fastener surface formed coextensively thereof, with the first hook and loop fastener surface arranged in confronting relationship relative to the right circular end wall, and a second flap including a second hook and loop fastener surface coextensively formed to the second flap in confronting relationship relative to the left circular end wall, and a first fastener patch mounted to the cylinder adjacent the right circular end wall diametrically opposed to the web, with the first fastener patch including a third hook and loop fastener surface cooperative with the first hook and loop fastener surface to secure the first flap to the first fastener patch, and a second fastener patch mounted to the cylinder aligned with the first fastener patch adjacent the left circular end wall diametrically opposed to the web, with a fourth hook and loop fastener surface formed coextensively to the second fastener patch for securement of the second flap to the second fastener patch.

3. An apparatus as set forth in claim 2 wherein the cylinder is transparent for visual observation of wires directed within the cylinder.

4. An apparatus as set forth in claim 3 wherein the first storage tube includes a first indicator formed to the cylinder for indication of a first wire directed within a first storage tube and a second indicator formed on the cylinder associated with the second storage tube for indication of a second wire directed within the second storage tube.

5. An apparatus as set forth in claim 4 wherein the first storage tube and the second storage tube are arranged parallel relative to one another in a spaced relationship.

6. An apparatus as set forth in claim 5 including a fifth hook and loop fastener surface formed to the web coextensively thereof opposed to the cylinder and the first hook and loop fastener surfaces.

* * * * *